United States Patent [19]

Galloway

[11] Patent Number: 4,738,667

[45] Date of Patent: Apr. 19, 1988

[54] PREFORMED CATHETER ASSEMBLY

[76] Inventor: Niall T. M. Galloway, 3211 Massdale Ave., Durham, N.C. 27707

[21] Appl. No.: 927,044

[22] Filed: Nov. 4, 1986

[51] Int. Cl.$^4$ .............................................. A61M 25/00
[52] U.S. Cl. ...................................... 604/281; 604/54
[58] Field of Search ..................................... 604/51–53, 604/158–170, 280–284

[56] References Cited

U.S. PATENT DOCUMENTS

| 3,680,562 | 8/1972 | Wittes et al. | |
|---|---|---|---|
| 3,782,381 | 1/1974 | Winnie | |
| 3,856,009 | 12/1974 | Winnie | |
| 3,860,006 | 1/1975 | Patel | |
| 3,920,023 | 11/1975 | Dye et al. | |
| 4,033,331 | 7/1977 | Guss et al. | 604/281 X |
| 4,248,224 | 2/1981 | Jones | |
| 4,563,181 | 1/1986 | Wijayarathna et al. | |
| 4,568,338 | 2/1986 | Todd | |
| 4,694,838 | 9/1987 | Wijayarthna et al. | 604/281 X |

OTHER PUBLICATIONS

"A Clinical Evaluation of a Modified Foley Catheter", by Rubino & Scialabba, *Journal of Obstetrics and Gynaecology*, May 1, 1983, pp. 103–104.

"A New Catheter for the Female Patient", by O'Neil et al., *Austalian and New Zealand Journal of Obstetrics and Gynaecology*, 1982, pp. 151–152.

"Coiled Tip Catheter for Measuring Intraversical Pressure", by Morita et al., *Urology*, Nov., 1986, p. 501.

*Primary Examiner*—Dalton L. Truluck
*Attorney, Agent, or Firm*—Richard Jenkins

[57] ABSTRACT

A catheter assembly which includes a catheter having a flexible, preformed distal end and a sheath slidably mounted thereon. The sheath can be slidably moved from a first position with the sheath overlying a portion of the catheter that is not precurved to a second position with the sheath overlying the precurved distal end in order to straighten the catheter for insertion and removal from a body cavity. When the catheter assembly is introduced into a body cavity, the distal end of the catheter is removed from the sheath in order to allow it to assume its preshaped form and thereby serve to retain the catheter. The distal end of the catheter is withdrawn into the sheath in order to remove the catheter from a body cavity.

12 Claims, 4 Drawing Sheets

PREFORMED CATHETER ASSEMBLY

TECHNICAL FIELD

The invention relates to a preformed catheter assembly, and more particularly, to a catheter assembly which allows for the safe introduction and removal of a preformed catheter from a body cavity and is also suitable for use in small children.

BACKGROUND ART

Catheters are well known in the art for fluid injection and/or removal from a human or animal body. Catheters are typically utilized to relieve urinary obstruction, to relieve severe urinary incontinence, and to monitor urine output in the critically ill patient.

A major problem with catheters has been their tendency to be displaced from the body. Although a number of solutions have been proposed to this problem, none has been entirely successful. For example, a common approach is to provide an expandable balloon at the distal end of the catheter which is inflated after placement of the catheter within a body cavity in order to retain it in position. This popular, self-retaining catheter is called a "Foley" catheter, but it suffers from shortcomings including the need for a separate channel within the catheter wall to inflate the balloon. This additional channel increases the diameter of the catheter and renders it unacceptable where very thin catheters are needed, such as for use in small children. Also, the balloon-type catheters can result in accidental urethral injury due to inflation of the balloon while in the urethra or by accidental extraction of the catheter without first deflating the balloon. The presence of the balloon can cause bladder spasms and discomfort. The large surface area of foreign material within the urinary bladder may promote crystal formation and result in bladder stones. Infection can result from use of balloon-type catheters since drainage from above the balloon allows a sump of urine to remain in the bladder at all times. Moreover, problems may arise with this type of catheter due to inability to deflate the balloon once inflated in a body cavity.

Another type of catheter commonly used is constructed of a flexible tubing which is preformed so that in its relaxed state in the body cavity it assumes a desired shape and is thereby self-retaining. A shortcoming of this catheter is that a stiffening member such as a wire is inserted through the bore of the catheter in order to straighten it for insertion into a body cavity. When the distal end reaches its destination, the wire is retracted and the preshaped distal end assumes its preformed shape. This approach to a self-retaining catheter possesses a number of shortcomings including the fact that the straightening wire is potentially dangerous and usage of the catheter is therefore confined to physicians. This is a substantial limitation to use of the catheter since many times it is desirable to have the catheter inserted by a nurse or technician.

SUMMARY OF THE INVENTION

The preformed catheter assembly of the present invention comprises a length of catheter tubing which is flexibly precurved at its distal end and includes one or more apertures therein. A sheath of a length less than the catheter tubing is slidably mounted thereover. The sheath can be moved from a first position with the sheath overlying a portion of the catheter tubing that is not precurved, to a second position with the sheath overlying the precurved distal end so that the catheter may be temporarily straightened to facilitate insertion and removal of the catheter tubing from a body cavity.

A principal object of the invention is to provide a self-retaining preformed catheter having a relatively small outer diameter which may be inserted safely and removed easily from a body cavity.

Another object of the invention is to provide a self-retaining catheter which is safe and simple to use.

A further object of the invention is to provide a self-retaining catheter which may be inserted and removed by a nurse or technician.

Another object of the invention is to provide a self-retaining catheter which may be safely inserted and removed by a nurse or technician in pediatric applications.

A still further object of the invention is to provide a self-retaining catheter which will conform to the shape of the male urethra.

DESCRIPTION OF THE DRAWINGS

Some of the objects of the invention having been stated, other objects will become evident as the description proceeds, when taken in connection with the accompanying drawings, in which.

DISCLOSURE OF THE INVENTION

Figure 1:
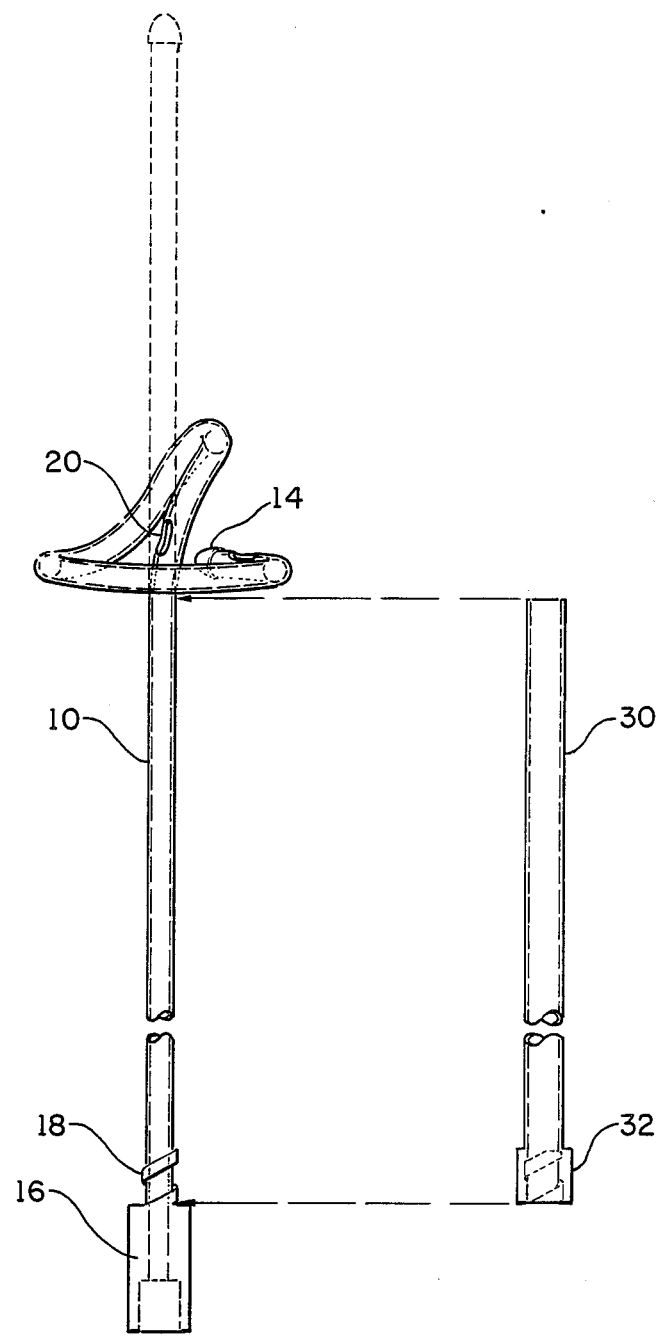
FIG. 1 is an elevational view of the catheter and the sheath of the preformed catheter assembly of the invention with the straightened shape of the catheter indicated in phantom lines.

Referring now more specifically to the drawings, the preformed catheter assembly of the invention includes a catheter 10 having an enlarged nose 14 at the distal end and a hub 16 at the proximal end. Nose 14 may define a number of other shapes which are appropriate for different clinical uses of the catheter assembly. Catheter 10 defines an externally threaded portion 18 at the proximal end thereof adjacent to hub 16. Catheter 10 is preferably made of a length of tubing which has a preformed shape to the distal end which will be assumed if this end of the catheter is allowed to relax. The preformed shape assumed in the relaxed state is indicated in solid lines in FIG. 1. Two apertures 20 are provided in catheter 10 although it should be appreciated that additional apertures may be utilized as a matter of design choice. Distal aperture 20 adjacent to nose 14 is desirable to allow immediate drainage upon placement in a fluid-filled body cavity in order to confirm correct placement of the catheter assembly. The preformed catheter assembly of the invention also includes sheath 30, which is adapted to be slidably mounted over catheter 10 so as to be moved from the proximal end to the distal end thereof as desired in order to straighten the preformed distal end of catheter 10 during insertion and removal of the catheter from a body cavity. Sheath 30 comprises an internally threaded proximal end 32 which may be threaded over portion 18 of catheter 10 in order to secure sheath 30 at the proximal end of catheter 10. It is contemplated that other means could also be utilized in order to secure sheath 30 to the proximal end of catheter 10. Thus, it can be appreciated that the preformed distal end of catheter 10 will form a desired three-dimensional shape in its relaxed state which will serve to retain the catheter in a body cavity. The purpose of slidably movable sheath 30 is to temporarily straighten the flexible, preformed distal end of catheter 10 for insertion and removal from a body cavity such as the urinary bladder.

Most suitably catheter 10 and sheath 30 are constructed of a biologically suitable material including polyester (e.g., DACRON by Dupont), polyurethane, and medical quality silicone. The preferred material is a blend of medical silicone (Nos. 4720, 4735 and 4750) manufactured by Dow Chemical. The catheter assembly is most suitably provided with a coating of a hydrogel material such as $B_n$—74 manufactured by C. R. Bard. The optimum size of the catheter assembly is 12–18 French for adults and 6–10 French for children. Also, as a matter of design preference, the catheter assembly may be radioopaque in order to facilitate X-ray imaging thereof.

Figure 2A:
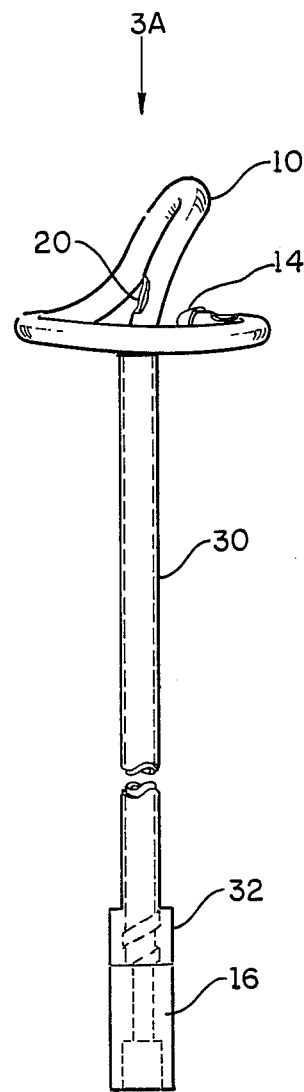
FIG. 2A is an elevational view of the preformed catheter assembly of the invention with the catheter in its first position with the sheath overlying a portion of the catheter which is not precurved.

FIG. 2A depicts the preformed catheter assembly of the invention as it would look when removed from a sterile package. It should be observed that sheath 30 threadingly engages catheter 10 and that the distal end of catheter 10 is in its preformed shape. As illustrated in FIGS. 1 and 2A, the preformed, relaxed shape of catheter 10 is in a spiral form and apertures 20 are provided through the wall thereof in order to drain fluid from a body cavity. As noted above, additional apertures 20 may also be provided along the length of the preformed distal end of catheter 10. It is preferable that apertures 20 be provided on the opposite side of the wall of catheter 10 from the spiral line of contact as sheath 30 slides along the preshaped distal end of catheter 10 in order to temporarily straighten the relaxed shape thereof. Otherwise, the leading edge of sheath 30 may possibly tend to lock upon contact with apertures 20.

Figure 2B:
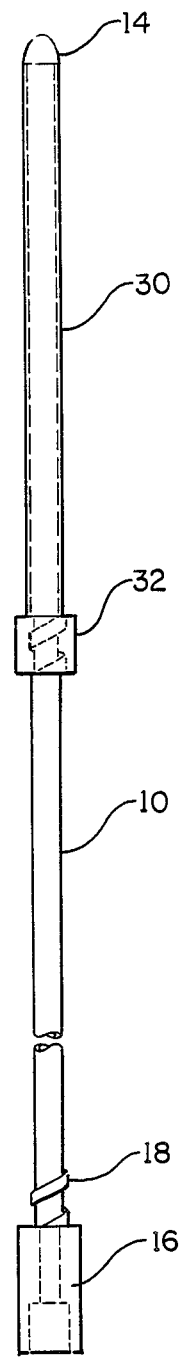
FIG. 2B is an elevational view of the catheter assembly of the invention with the catheter having been slidably moved to a second position with the sheath overlying the precurved distal end of the catheter.

FIG. 2B shows the preformed catheter assembly with sheath 30 having been unscrewed and sheath 30 advanced or catheter 10 slidably withdrawn so that sheath 30 has been slidably advanced toward the distal end of catheter 10 in order to straighten the preshaped distal end thereof for insertion into a body cavity. Sheath 30 is retained on catheter 10 by nose 14 which it abuts when sheath 30 has been fully advanced. In a typical application of the inventive catheter, the assembly as shown in FIG. 2B would be advanced into the urethra of a patient to the level of hub 16. Catheter 10 is then advanced through sheath 30 so that it may assume its preformed relaxed shape in the bladder and thereby be retained. Sheath 30 is then screwed or otherwise secured to catheter 10. The catheter assembly would then be drawn gently back to the neck of the bladder. A conventional external collecting system for continuous drainage or a valve for intermittent drainage may be attached to hub 16. When removal of the catheter is desired, the process is reversed and catheter 10 would be released (by unscrewing sheath 30) and withdrawn into sheath 30 and the entire assembly removed from the patient's urethra. Although described immediately above for use in the bladder, other applications are contemplated including use as a nephrostomy tube for the kidney, pleural drainage of the chest, lymphocele or abscess cavity drainage of the abdomen, and peritoneal drainage or use as a temporary peritoneal dialysis catheter. Veterinary applications are also possible for the catheter assembly.

Figure 3A:
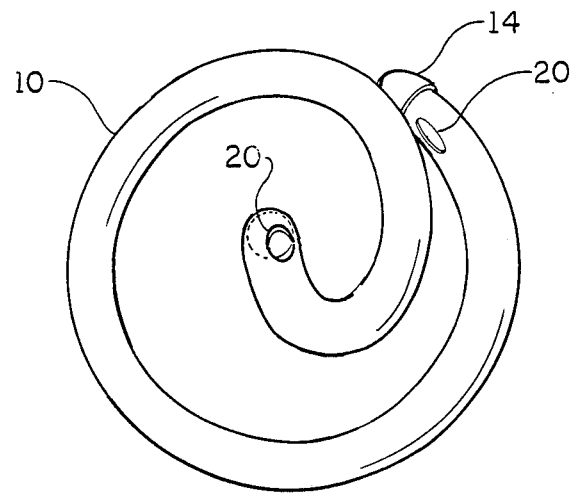
FIG. 3A is an enlarged plan view of the catheter.
Figure 3B:
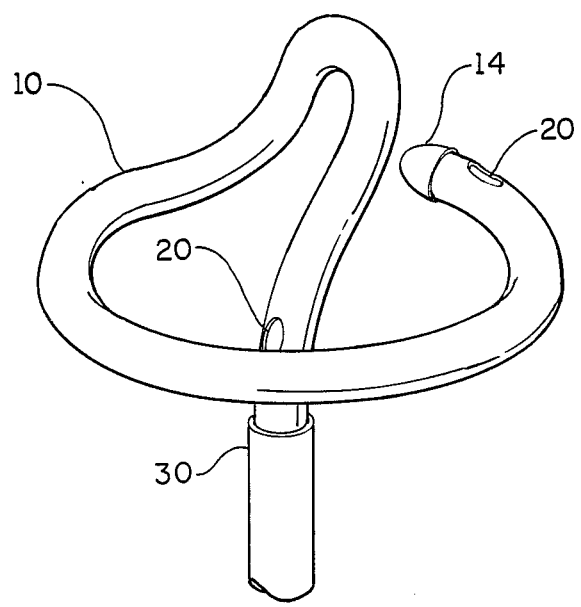
FIG. 3B is an enlarged fragmentary perspective view of the catheter to better show its preferred shape.
Figure 4:
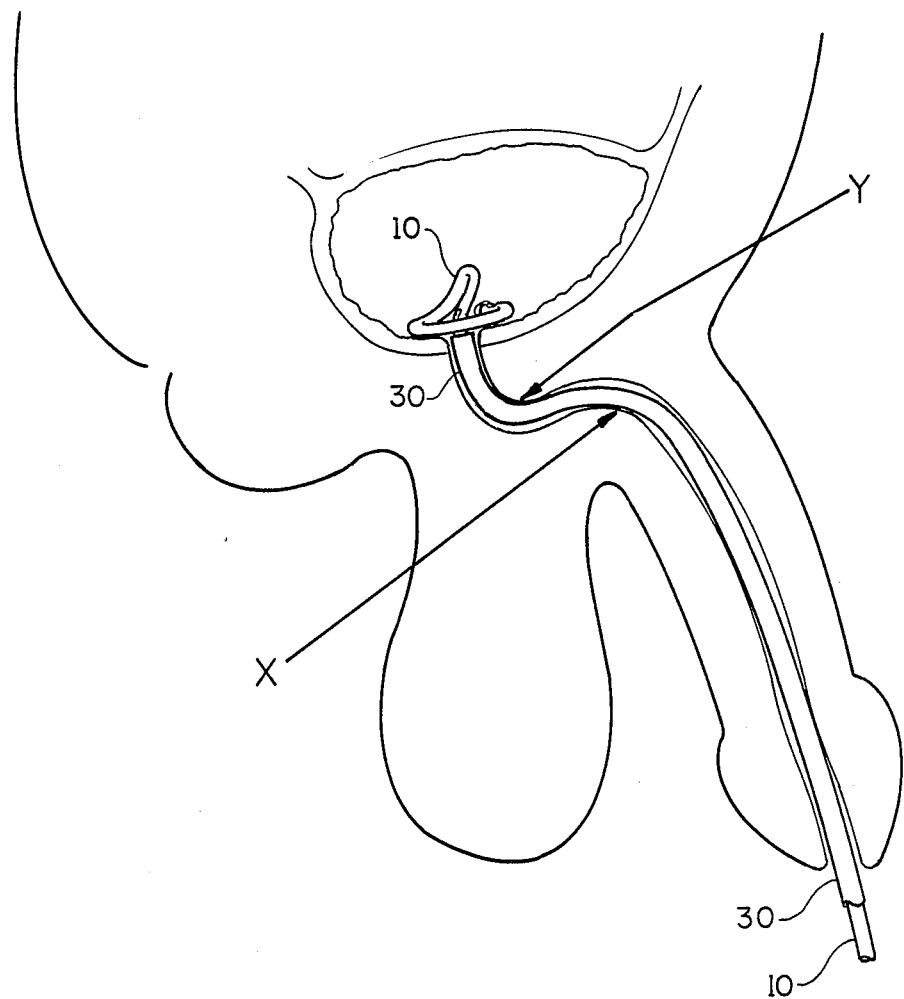
FIG. 4 is a diagrammatic view of the catheter assembly of the invention positioned in the male urethra and bladder.

In FIGS. 3A and 3B the preferred spiral shape of the preformed distal end of catheter 10 is illustrated in greater detail. This particular shape consists of a relatively gradual curve of the distal end of the catheter of about 120 degrees or more throughout the shaped length. This relaxed shape allows for an easy advancement of sheath 30 slidably mounted thereon in order to straighten the curved distal portion of the catheter to facilitate insertion and removal from a body cavity. With reference now to FIG. 4, the catheter assembly is shown properly positioned in the male urethra and bladder with catheter 10 being retained in place by the spiral shape of the preformed distal end thereof. Another embodiment of applicant's catheter assembly provides a flexible "S" pre-shaped sheath which conforms to the natural shape of the male urethra. This allows for the catheter assembly to be used without forming areas of pressure necrosis (X and Y in FIG. 4) within the urethra at the two natural curves in the urethral pathway, as experienced with conventional catheters.

It will thus be seen that there has been described above a catheter assembly which is of inexpensive and safe construction and overcomes shortcomings known to exist with catheters presently being utilized. Moreover, a nurse or technician may insert and remove the catheter assembly of the invention in view of the relative safety associated with its use.

It will be understood that various details of the invention may be changed without departing from the scope of the invention. Furthermore, the foregoing description is for the purpose of illustration only, and not for the purpose of limitation—the invention being defined by the claims.

What is claimed is:

1. A preformed catheter assembly for insertion into a body cavity and comprising:
    a length of non-bifurcated catheter tubing being flexibly pre-curved into a spiral form at its distal end and wherein the end portion of said distal end is radially enlarged, said tubing defining at least one aperture in the wall thereof; and
    a generally elongate sheath of a length less than said catheter tubing and being slidably mounted thereover so said sheath may be moved from a first position with said sheath overlying a portion of said catheter tubing that is not pre-curved to a second position with said sheath overlying said pre-curved distal end, said radially enlarged end portion serving as a stop for said sheath when it is moved from said first position to said second position;
whereby said sheath may be moved from said first position to said second position to temporarily straighten said distal end of said catheter tubing for ease of insertion and removal of said catheter tubing from a body cavity.

2. A catheter assembly according to claim 1 wherein securement means are provided for maintaining said sheath in said first position.

3. A catheter assembly according to claim 2 wherein said securement means comprises a threaded portion defined along an external portion of the proximal end of said catheter tubing which is adapted to engage an integrally threaded portion defined within the proximal end of said sheath.

4. A catheter assembly according to claim 1 wherein said catheter tubing and said sheath are constructed of a plastic-like material.

5. A catheter assembly according to claim 4 wherein said catheter assembly is radioopaque.

6. A catheter assembly according to claim 4 wherein said sheath is constructed of a flexibly precurved material which will assume the natural "S" shape of the male urethra in its relaxed state.

7. A catheter assembly according to claim 1 wherein a plurality of apertures are defined in the wall of said precurve distal end.

8. A catheter assembly according to claim 7 wherein said plurality of apertures are located on the opposite side of the wall of said precurved distal end from the contact pathway of said sheath with said distal end as said sheath is moved from said first position to said second position.

9. A method for insertion of a catheter into a body cavity or the like comprising the steps of:
providing a catheter assembly comprising a length of non-bifurcated catheter being flexibly pre-curved into a spiral form at its distal end and wherein the end portion of said distal end is radially enlarged, said catheter having a sheath slidably mounted thereover so said sheath is movable from a first position with said sheath overlying a portion of said catheter that is not pre-curved to a second position with said sheath overlying said pre-curved distal end, said radially enlarged end portion thereby serving as a stop for said sheath when it is moved from said first position to said second position;
slidably moving said sheath from said first position to said second position in order to temporarily straighten said distal end of said catheter;
advancing said catheter assembly into a body cavity; and
slidably moving said catheter forward in said sheath from said second position to said first position in order to allow said distal end to assume its pre-curved shape and thereby retain said catheter end in the body cavity.

10. A method according to claim 9 including the step of securing said sheath in said first position after said distal end has assumed its precurved shape in the body cavity.

11. A method according to claim 9 including the step of slidably moving said catheter from said first position back to said second position to temporarily straighten said distal end prior to removal of said catheter assembly from the body cavity.

12. A preformed catheter assembly for insertion into a body cavity and comprising:
a length of catheter tubing being flexibly pre-curved at its distal end and defining at least one aperture in the wall thereof;
a generally elongate sheath of a length less than said catheter tubing and being slidably mounted thereover so said sheath may be moved from a first position with said sheath overlying a portion of said catheter tubing that is not pre-curved to a second position with said sheath overlying said pre-curved distal end; and
securement means for maintaining said sheath in said first position and comprising a threaded portion defined along an external portion of the proximal end of said catheter tubing which is adapted to engage an internally threaded portion defined within the proximal end of said sheath.

* * * * *